US010287570B2

(12) United States Patent
Qian

(10) Patent No.: US 10,287,570 B2
(45) Date of Patent: May 14, 2019

(54) SYSTEM AND METHOD FOR COLLECTING A SAMPLE OF NUCLEIC ACID

(71) Applicant: OCCAM BIOLABS, INC., Newark, DE (US)

(72) Inventor: Mingwei Qian, Hockessin, DE (US)

(73) Assignee: OCCAM BIOLABS, INC., Newark, DE (US)

( * ) Notice: Subject to any disclaimer, the term of this patent is extended or adjusted under 35 U.S.C. 154(b) by 88 days.

(21) Appl. No.: 15/528,300

(22) PCT Filed: Nov. 20, 2015

(86) PCT No.: PCT/US2015/061917
§ 371 (c)(1),
(2) Date: May 19, 2017

(87) PCT Pub. No.: WO2016/081860
PCT Pub. Date: May 26, 2016

(65) Prior Publication Data
US 2017/0335313 A1 Nov. 23, 2017

Related U.S. Application Data

(60) Provisional application No. 62/082,830, filed on Nov. 21, 2014.

(51) Int. Cl.
*G01N 1/00* (2006.01)
*C12N 15/10* (2006.01)
(Continued)

(52) U.S. Cl.
CPC .......... *C12N 15/1017* (2013.01); *B01L 3/502* (2013.01); *C12Q 1/6806* (2013.01);
(Continued)

(58) Field of Classification Search
CPC ....................................................... G01N 1/40
See application file for complete search history.

(56) References Cited

U.S. PATENT DOCUMENTS 5,234,809 A 8/1993 Boom et al.
5,346,994 A 9/1994 Chomczynski
(Continued)

FOREIGN PATENT DOCUMENTS

CN 102481576 A 5/2012
CN 202538808 U 11/2012
(Continued)

OTHER PUBLICATIONS

International Search Report and Written Opinion for International Application No. PCT/US2015/061917, dated Feb. 5, 2016—8 Pages.
(Continued)

*Primary Examiner* — Jyoti Nagpaul
(74) *Attorney, Agent, or Firm* — RatnerPrestia

(57) ABSTRACT

A system for collecting biomolecules comprising an extractor assembly comprising a top cap, an extractor core, an extractor core adaptor, an extractor body having an internal volume, and a bottom cap ring. The top cap comprises a sample connection port and is configured to be secured to the extractor body by the bottom cap ring. The extractor core is adapted to be removably attached to a connection interface of the top cap and contains a substrate for collecting the biomolecules. The extractor core adaptor has an upstream open end for mating with the downstream end of the extractor core and a downstream protrusion configured to project through an opening in the extractor body. Methods for using the system to collect samples for transport and further processing to detect disease are also disclosed.

20 Claims, 10 Drawing Sheets

(51) Int. Cl.
*C12Q 1/6806* (2018.01)
*G01N 1/40* (2006.01)
*B01L 3/00* (2006.01)

(52) U.S. Cl.
CPC .............. *G01N 1/40* (2013.01); *B01L 3/5082* (2013.01); *B01L 2200/026* (2013.01); *B01L 2200/0631* (2013.01); *B01L 2200/0689* (2013.01); *B01L 2200/185* (2013.01); *B01L 2300/042* (2013.01); *B01L 2300/046* (2013.01); *B01L 2300/0681* (2013.01); *B01L 2300/0832* (2013.01); *B01L 2300/123* (2013.01); *G01N 2001/005* (2013.01)

(56) References Cited

U.S. PATENT DOCUMENTS

| | | | |
|---|---|---|---|
| 6,375,855 | B1 | 4/2002 | Vassarotti |
| 6,720,417 | B1 | 4/2004 | Walter |
| 7,282,371 | B2 | 10/2007 | Helftenbein |
| 7,862,773 | B2 | 1/2011 | Ibrahim |
| 7,897,378 | B2 | 3/2011 | Block et al. |
| 8,158,349 | B2 | 4/2012 | Block et al. |
| 8,216,832 | B2 | 7/2012 | Battrell et al. |
| 8,377,715 | B2 | 2/2013 | Suh et al. |
| 8,685,742 | B2 | 4/2014 | Singer |
| 8,927,261 | B2 | 1/2015 | Block et al. |
| 8,999,268 | B2 | 4/2015 | Egger-Cimenti et al. |
| 2003/0088963 | A1 | 5/2003 | Mayer |
| 2005/0227269 | A1 | 10/2005 | Lloyd, Jr. et al. |
| 2007/0092403 | A1 | 4/2007 | Wirbisky et al. |
| 2007/0202538 | A1 | 8/2007 | Glezer et al. |
| 2008/0017577 | A1 | 1/2008 | Yi et al. |
| 2009/0246877 | A1 | 10/2009 | Moran, Jr. |
| 2010/0200509 | A1 | 8/2010 | Suh et al. |
| 2010/0274155 | A1 | 10/2010 | Battrell et al. |
| 2011/0056893 | A1 | 3/2011 | Leach et al. |
| 2012/0225001 | A1 | 9/2012 | Koeda |
| 2012/0291872 | A1 | 11/2012 | Brady et al. |
| 2013/0037509 | A1 | 2/2013 | Rahimy et al. |
| 2014/0011229 | A1 | 1/2014 | Nakatsuka et al. |
| 2014/0147851 | A1 | 5/2014 | Qian |
| 2016/0097049 | A1 | 4/2016 | Qian |

FOREIGN PATENT DOCUMENTS

| | | |
|---|---|---|
| CN | 102811693 A | 12/2012 |
| JP | H03123837 A | 5/1991 |
| JP | 1996508395 A1 | 2/1994 |
| JP | H07103869 A | 4/1995 |
| JP | 2001511644 A | 8/2001 |
| JP | 2007529210 A | 10/2007 |
| RU | 2244559 C2 | 1/2005 |
| WO | 9403103 A1 | 2/1994 |
| WO | 2004011122 A2 | 2/2004 |
| WO | 2005090567 A1 | 9/2005 |
| WO | 2005102526 A1 | 11/2005 |
| WO | 2010101865 A1 | 9/2010 |
| WO | 2013003309 A1 | 1/2013 |
| WO | 2013114220 A2 | 8/2013 |
| WO | 2014190249 A1 | 11/2014 |

OTHER PUBLICATIONS

Preliminary Report on Patentability for International Application No. PCT/US2015/061917, dated May 23, 2017—8 Pages.
Chinese Office Action for Chinese Application No. 2014800420434.4, dated Nov. 4, 2016, including English translation, 18 Pages.
Extended European Search Report for European Application No. 14801362.6, dated Feb. 9, 2017—7 Pages.
International Preliminary Report on Patentability (Chapter 1 of the Patent Cooperation Treaty) for International Application No. PCT/US2014/039320, dated Nov. 24, 2015—9 Pages.
International Search Report for International Application No. PCT/US2014/039320, dated Oct. 22, 2014—3 Pages.
QIAamp Circulating Nucleic Acid Handbook, Second Edition, Jan. 2011, pp. 1-56.
Written Opinion of the International Searching Authority for International Application No. PCT/US2014/039320, dated Oct. 22, 2014—8 Pages.
Russian Official Action for Russian Application No. 2015155282/10(085250), dated Oct. 10, 2017 with translation14 pages.
Second Chinese Office Action for Chinese Application No. 201480042043.4, dated Sep. 1, 2017, including English translation, 13 pages.
Entire patent prosecution history of U.S. Appl. No. 14/892,709, filed Nov. 20, 2015 entitled "System and Method for Collecting a Sample of Nucleic Acid".
Extended European Search Report for European Application No. 15 860 729.1, dated May 24, 2018, 7 pages.
Non Final Office Action for U.S. Appl. No. 14/892,709, dated Aug. 28, 2018, 53 pages.
Notice of Reasons for Rejection for Japanese Application No. 2016-515112, dated Apr. 3, 2018, including English translation, 4 pages.
Notice of Allowance for U.S. Appl. No. 14/892,709, dated Mar. 21, 2019, 10 pages.

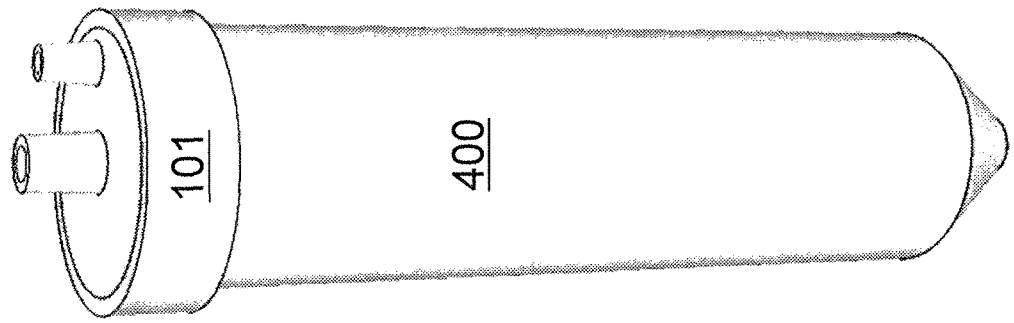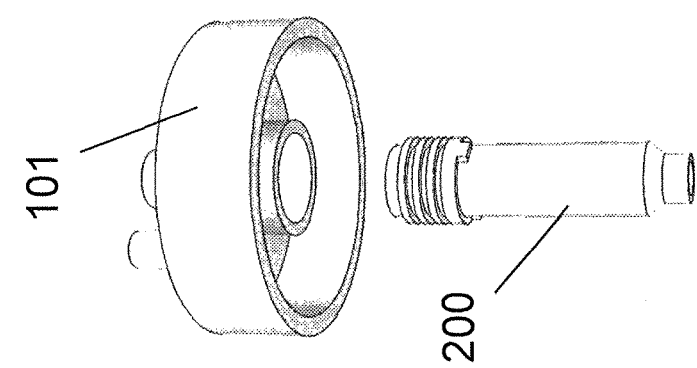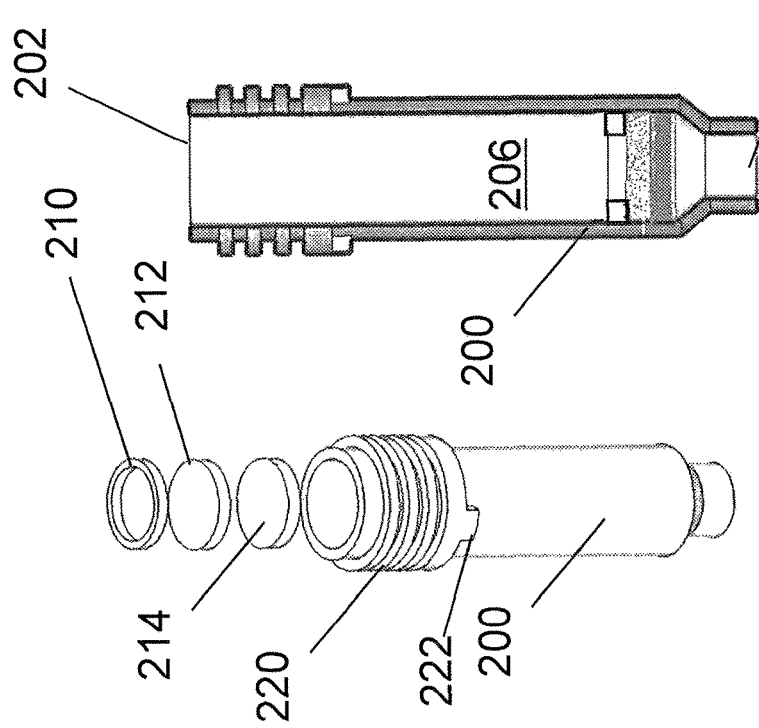

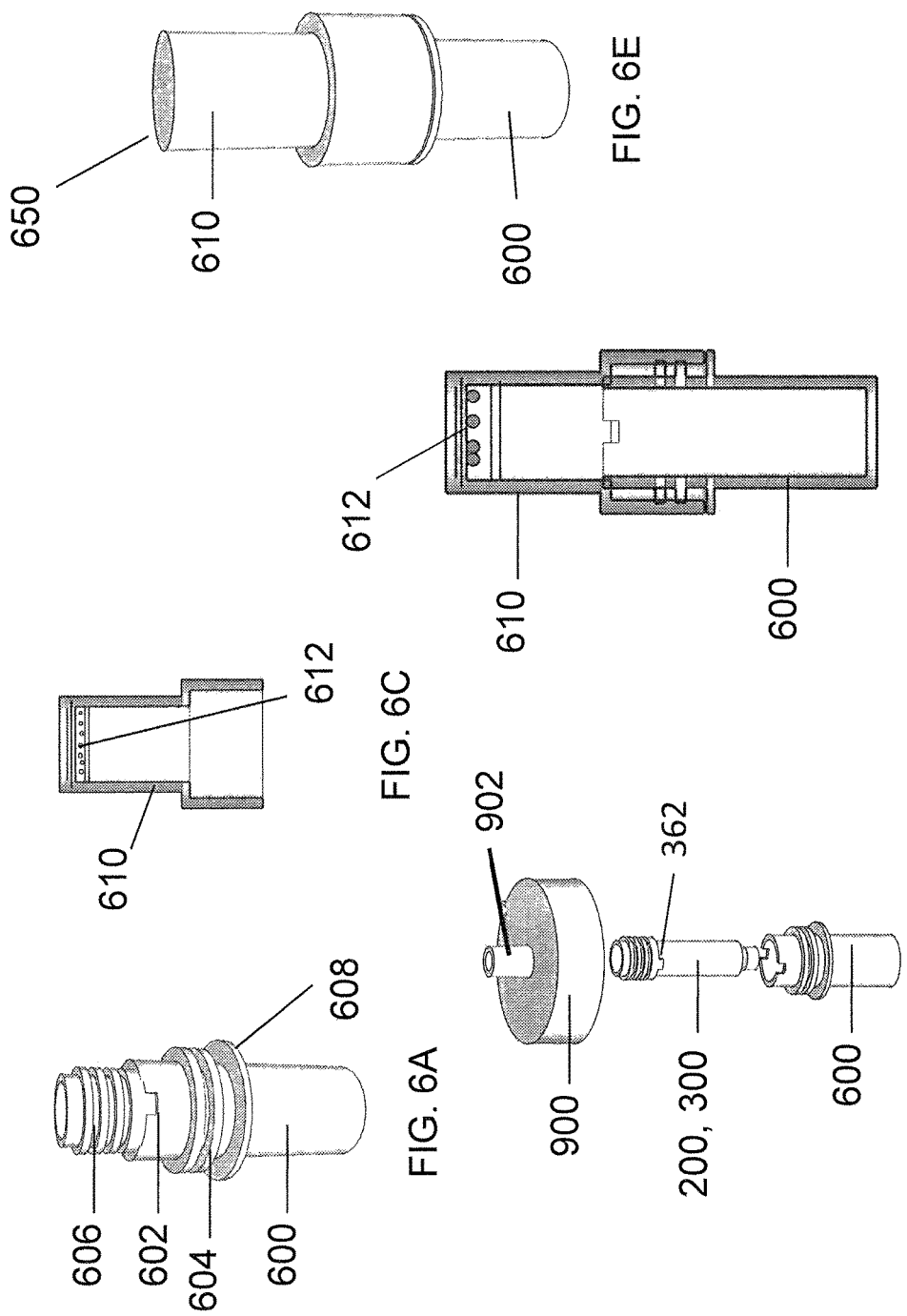

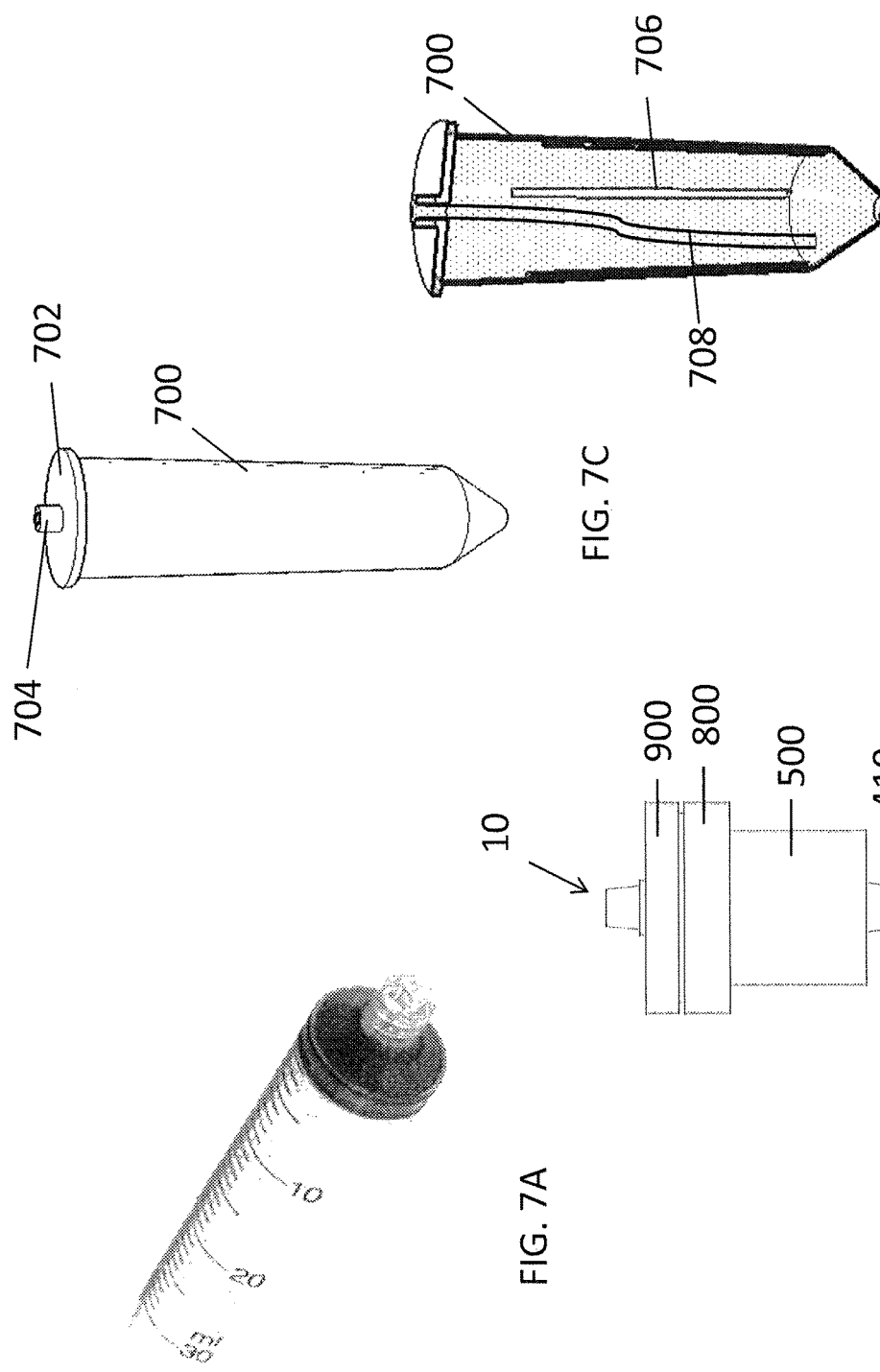

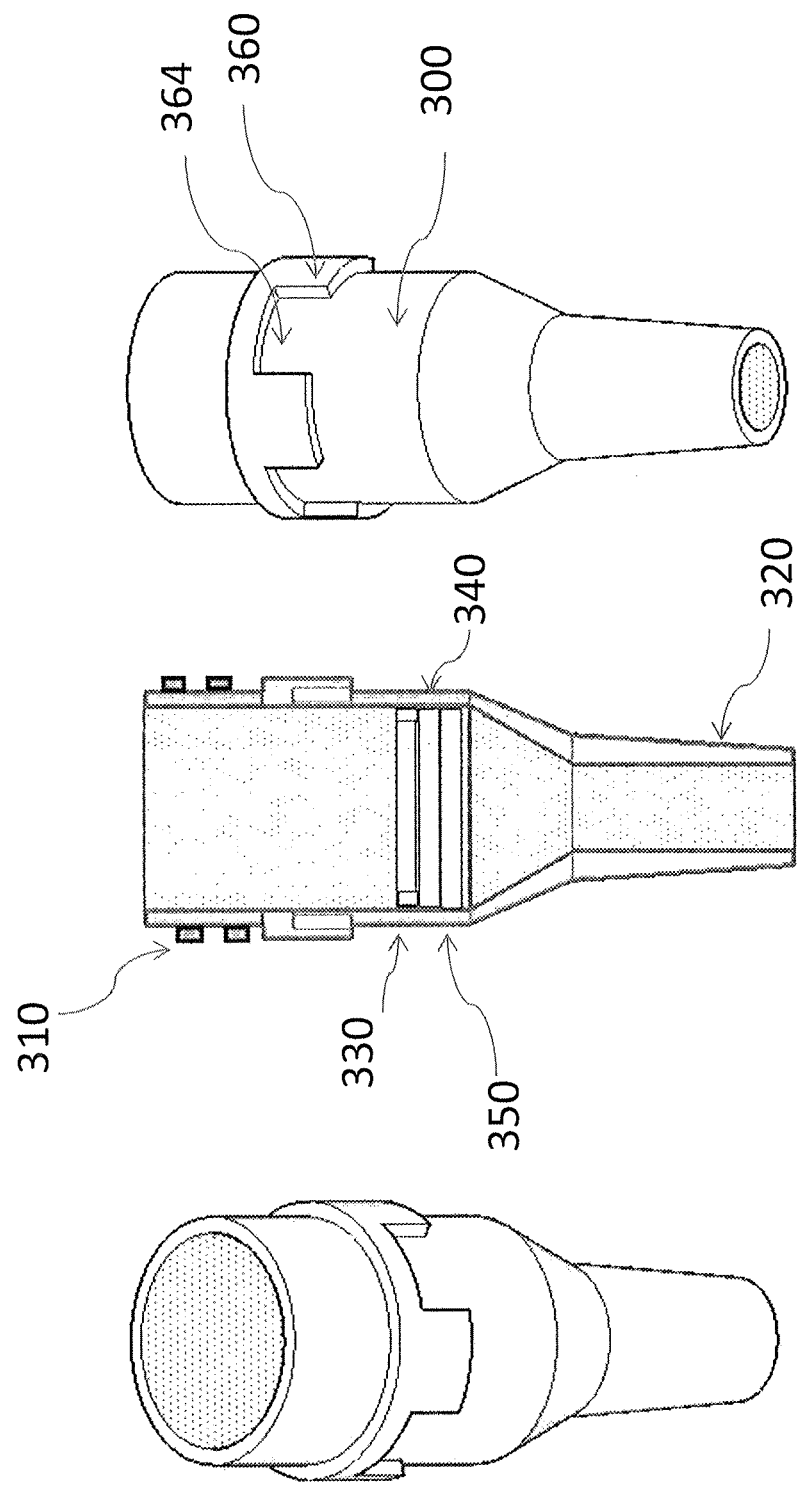

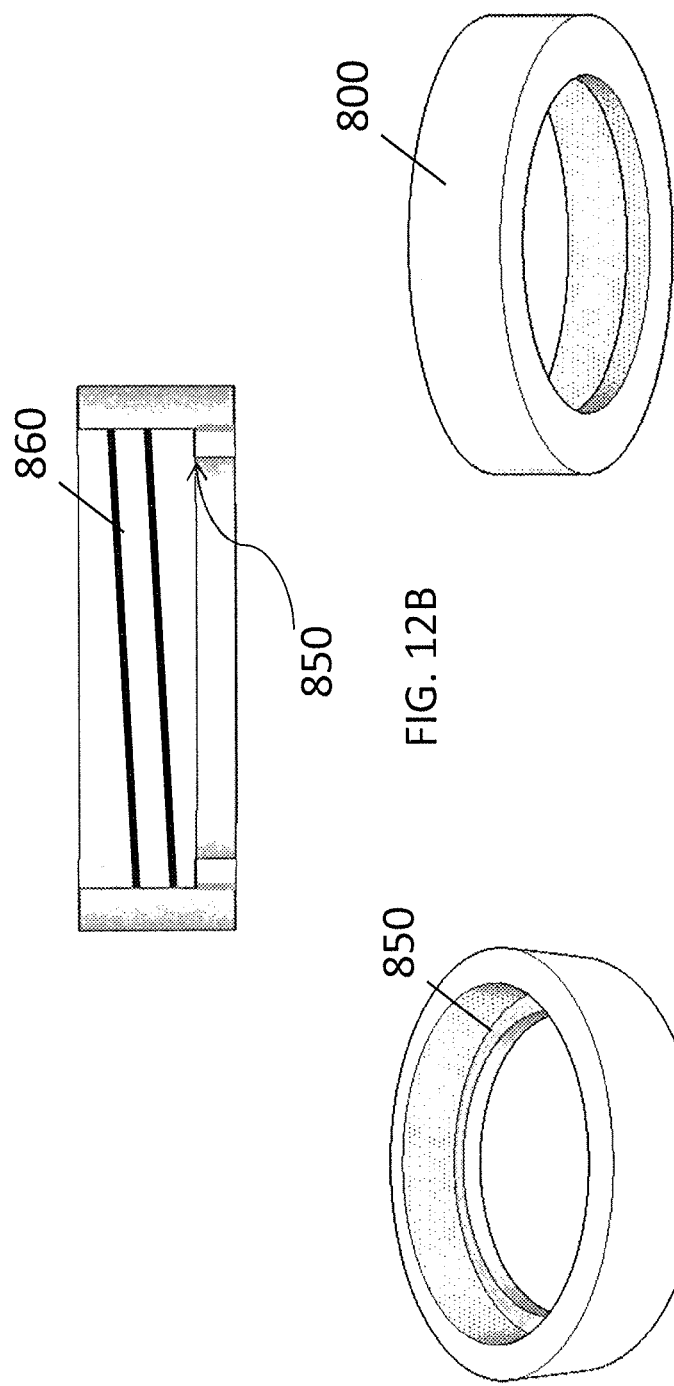

SYSTEM AND METHOD FOR COLLECTING A SAMPLE OF NUCLEIC ACID

CROSS REFERENCE TO RELATED APPLICATIONS

This Application is the National Stage filing of International Appln. NO. PCT/US2015/061917, filed Nov. 20, 2015, which itself claims priority to U.S. Provisional Application Ser. No. 62/082,830, titled BIOMOLECULE EXTRACTION SYSTEM, filed Nov. 21, 2014, which is hereby incorporated by reference in its entirety.

BACKGROUND OF THE INVENTION

Current systems and methods for collection, extraction, and detection of nucleic acid from biological samples for testing are typically complicated, requiring multiple steps with technically trained personnel, and not optimized for processing samples with large volumes or for preventing cross-contamination in sample processing and stabilization for shipment.

A variety of body fluids, such as blood, plasma, serum, Cerebrospinal fluid (CSF), pleural effusion, ascites, urine etc., contain short chain nucleic acid (NA) fragments, namely, cell-free nucleic acids (cfNA), or circulating nucleic acids (cNA). Altered nucleic acids, originated endogenously from a tumor, or "exogenously" from fetus or pathogenic infection inside the body, may present as cfNA in the peripheral blood at very low concentrations and may be detectable, and further, be distinguishable from normal host cfNA. Extraction of sufficient amount of those cfNA from plasma or serum for testing requires processing a relatively large volume of fluid, which imposes a unavoidable technical challenge in clinical diagnostic settings. Accordingly, there is a need the field for new methods to meet such challenges.

Exemplary such methods for detecting, for example, tuberculosis, are described in Pending PCT published application WO2012135815, invented by the inventor of this application, and incorporated herein by reference. Such testing, however, may be most useful in regions of the world lacking ready access to the expensive processing equipment used in analysis of the samples. Accordingly, there is a need in the art for a collection system and methodology that will permit capturing nucleic acid in sufficient amounts from large volume biological samples, to run later analysis, to prevent contamination from the environment and operators, and to preserve and ship the nucleic acid, so that nucleic acid can be collected at a point of care facility using relatively inexpensive equipment, and then shipped in a stabilized form to a central location for further processing and assays.

Various methods of extraction suitable for isolating circulating DNA or RNA from large volumes of biological fluids are known, such as those described, for example, in QIAamp® Circulating Nucleic Acid Handbook, ($2^{nd}$ edition, 02, 2011, Qiagen), and an improved spin column extraction method described in U.S. Pat. No. 8,685,742, based on technological principles from U.S. Pat. No. 5,234,809 (Boom technology). U.S. Pat. No. 5,346,994 describes a technology an organic liquid extraction method using phenol-chloroform. Both of these methods may be used for large volume extraction, such as from plasma or serum specimens, but the organic reagents are toxic, which limits its use. Both of the technologies mentioned above require a high-speed centrifuge (>10,000 G), though elution or precipitation, to obtain the extracted NA for downstream applications.

Also, U.S. Pat. Nos. 7,897,378 and 8,158,349 describe devices and method for purifying or isolating nucleic acids from larger sample volumes, including systems comprising a pair of cooperating hollow bodies through which samples are passed into a collection vessel, with nucleic acids bound to a binding material in one of the hollow bodies. The hollow body containing the retained sample is transferred to a first receiving vessel for washing, then the purified or isolated nucleic acids are eluted and collected in a second receiving vessel for further analysis. Again, a high-speed centrifuge is required for eluting bound nucleic acids from the solid phase matrix.

U.S. Pat. No. 5,234,809 (Boom), for example, incorporated herein by reference, discloses a method for isolating nucleic acids, which is suitable for a multiplicity of different uses. It describes a method for isolating nucleic acids from nucleic acid-containing starting materials by incubating said starting material with a chaotropic buffer and a DNA-binding solid phase. The chaotropic buffers effect, if necessary, both lysis of the starting material and binding of the nucleic acids to the solid phase.

A novel biomolecule extraction system was first described by the Applicant in U.S. Provisional Patent Application Ser. No. 61/827,244 and PCT Application Ser. No. US14/39320 ("the Original Applications"), both of which are incorporated herein by reference in their entireties. The Original Applications disclosed inventions relating to methods and systems for processing a biological sample, namely lysing, binding, washing, stabilizing and eluting biomolecules of the biological sample. One embodiment included a system for collecting a sample of nucleic acid, the system comprising a receptacle defining an internal volume, a removable cap for the receptacle and having a connection interface in fluid communication with a sample connection port in the cap, a filter column adapted to be removably attached to the connection interface of the receptacle cap, a sample collection container, and a shipping container. Various other components of the system were disclosed. The Original Applications also disclosed a method for collecting a sample of nucleic acid, the method comprising the steps of: (a) providing the collection system described herein; (b) collecting a volume of sample-containing fluid in the sample collection container; (c) connecting the sample collection container to the receptacle via the sample collection port; (d) passing the volume of sample-containing fluid from the sample collection container through the filter column, thereby collecting the sample on the substrate and collecting a remainder in the receptacle; (e) placing the shipping container open end over the filter column, engaging the filter column with the shipping container, and detaching the filter column from the receptacle cap and (f) temporarily sealing the shipping container with the removable lid. The disclosed methods are particularly useful for processing the collected nucleic acid at minimally-equipped medical-care settings, such as small, remote and/or peripheral clinics, and shipping the collected samples to a better-equipped central laboratory for further analysis of the collected samples for detection of a disease, such as for detection of latent tuberculosis.

As molecular technologies rapidly advance, biomarker detection of circulating cell-free nucleic acids (NA) including cell-free DNA and cell-free RNA (cfDNA and cfRNA) respectively, or together (cfNA or cNA) in plasma, serum and other body fluids is emerging as less invasive means for diagnosis and prognosis of prenatal genetic abnormalities, cancers, solid organ transplantation rejection and infectious diseases such as tuberculosis, from early discoveries. However, due to extremely low abundance in body fluids, cfNA as clinical analyte is still facing various technical issues that affect cfNA sample quality, quantity, and consequently the final diagnostic results. Technical issues include: 1) sample collection/transportation, 2) sample processing, and 3) the potential opportunity using cfRNA for disease status monitoring.

Sample Collection/Transportation Issues

Most accessible sources of cfNA are plasma or serum (together PS) of peripheral blood. Plasma concentrations of cfNA in normal individuals are very low, in the range of 1.8-44 ng/ml or about 500-10000 genome equivalents/ml (ge/ml). The trace amount of tumor-derived cfNA or circulating tumor NA (ctNA) in PS, if exists, may be merely one to a few hundred copies per ml, or about 0.005-0.01% of total cfNA (4). In order to collect sufficient target ctNA, a large volume of PS, i.e. 1-5 ml is often needed. In addition, release of even small percentage of cellular DNA or RNA from blood will cause difficulties in downstream analysis of the targeted cfNA. To prevent cfNA degradation and genomic NA (gNA) release from blood cells, separation of the PS from blood cells should typically take place within 2 hours, 2-4 hours or within 7 hours after phlebotomy based on different protocols. Separation usually requires 1 step or 2 steps of centrifugation at 1000-2000 g for 10 minutes and optionally, 5000-16000 g. Separation of serum by simple centrifugation after blood clotting may be easier, but may introduce a predictable degree of cell lysis due to clotting that may not significantly affect final analysis. Though the concentrations of targeted ctDNA in plasma and serum are about the same, it is noticed that serum contains more large gDNA fragments, possibly released from blood cells during clotting.

Another issue of sample collection is temperature. The PS after separation from blood cells typically needs to be stored at −20 C (for short time) or −80 C (for long time). Sample collection sites such as phlebotomy sites are not always in close proximity to the molecular diagnostic facility. Thus, cryopreservation of frozen PS during transportation typically needs to be maintained. Novel blood collection devices, Cell-Free DNA BCT™ (BCT) and Cell-Free RNA BCT, were developed by Streck Inc. (NE). They prevent cellular DNA and RNA release and stabilize cfDNA and cfRNA in blood at ambient temperature for up to 7 days and 2 days respectively. The BCT technology partially solves the issues of separation delay and the transportation condition. However, it still faces the obstacles of sample processing to be performed in the molecular diagnostic facility, as described below.

Sample Processing Issues

The clinical applications of cfNA testing are also hindered by sample processing, i.e., efficient extraction, enrichment, and recovery of trace fragile cfNA from large volume of same fluids. Nucleic acid extraction and purification from biological materials is generally based on two approaches: organic extraction and solid phase absorption. The organic extraction, namely, guanidine thiocyanate-phenol/chloroform method, is applicable for large volume of biological fluids such as PS, but not as suitable for use in a clinical laboratory, due to toxicity of reagents and multiple hands-on processing steps. Solid phase extraction, based on Boom technology, has been progressively developed into two major formats: column (or spin column) and magnetic bead technologies. The basic principle is that high concentrated chaotropic agents disrupt second and third structures of proteins and lipid complexes, inactivate enzymes-including DNA and RNA nucleases, and release nucleic acids from bound microstructures (Lysing). Adding alcohol into the lysate facilitates binding of the free nucleic acids to an absorbent matrix (Binding). In the column (spin column) format, a lysate-binding mixture is added into a microcolumn and flows through porous matrix (i.e., silica membrane) by centrifugation or vacuum. DNA or RNA in the mixture is absorbed on the matrix and the rest (waste) is removed. Then, 1-2 step(s) of washing are typically performed to remove residue contaminant (Washing). Finally, the bound nucleic acids are released from the matrix and are collected to a new tube by centrifugation (Eluting). Automation of spin column operation is not easy; however, an automated instrument (QIAcube) specifically for spin columns has been developed recently (Qiagen). Processing a sample with a spin column typically requires four to five times repeated centrifugation, such as with a high speed desktop centrifuge. With a vacuum apparatus, the centrifugation may be reduced to one step (elution), but multiple pipettings are still necessary. Spin columns are generally designed to process small volume samples, often <300 µl. A popular kit, QIAamp® DNA Blood Mini kit (DBM, Qiagen) has been extensively used for fetal cfDNA or ctDNA extraction from maternal blood. The volume capacity of spin columns is believed to limit its use in cfNA extraction for sensitivity-demand studies.

Another specifically designed kit for cfNA extraction is Qiagen's QIAamp® circulating Nucleic acid kit (Q-CNA kit), which comprises an extension tube, as described in U.S. Pat. No. 8,685,742, the contents of which are hereby incorporated by reference. A Q-CNA kit features several advantages: 1) it has extendable capacity for the sample volume (1-5 ml), 2) it is vacuum-enabled, and, particularly 3) it is formulated for recovery of short cfNA fragments in PS. In a recent stringent comparison study, it was found recovery of short DNA (115 pb and 461 bp) with Q-CNA kit is 3-4 times more than that with Qiagen's DBM kit (24). Though Q-CNA kit has been adopted with increasing popularity in cfNA extraction for quantitative PCR (qPCR), digital PCR (dPCR), and next generation sequencing (NGS) applications in tumor diagnosis and non-invasive prenatal test (NIPT), there are still several issues to prevent it from being widely used in clinical setting: 1) multiple-repeated pipetting steps raise the question of possible mis-pipetting and cross-contamination; 2) the Q-CNA is configured for use with a vacuum manifold QIAvac™ 24 Plus (Qiagen) powered by a vacuum pump, so in operation, the sample tubes are exposed to air and subjected to alternating negative pressure; therefore, contamination from environment may occur; 3) furthermore, inconsistent flow rate and occasionally lysate-binding mix clogs on the porous silica membrane may cause uneven flow and/or may completely block flow-through; 4) finally, to elute the solid-phase-bound CNA, a high speed centrifugation is still inevitable. Thus, all above mentioned methods require certain equipment and electricity supply.

Silica coated magnetic bead (MB) technology is based on the same principle and has similar steps as described above. Unlike the column format in which the absorbent is fixed in the column, magnetic beads are dispensed into the lysate and collected with magnetic field. Operation of MB processing is relatively easy due to automation. Several manufacturers provide multiple models tailored to specific needs, but, most of them have a sample volume capacity limited to 1 ml.

Thus, a need remains for systems and methods addressing one or more of the foregoing issues, and that improve upon and providing alternative embodiments to the collection systems described in the Original Applications.

SUMMARY OF THE INVENTION

One aspect of the invention comprises a system for collecting biomolecules. In one embodiment, the system comprises an extractor assembly comprising a top cap, an extractor core, an extractor core adaptor, an extractor body having an internal volume, and a bottom cap ring. The top cap is adapted to be removably secured to the extractor body with the bottom cap ring, the top cap having an internal side facing the internal volume of the extractor body and an external side facing away from the extractor body. The top cap comprises a sample connection port communicating between the internal side and the external side, the cap having no other orifices communicating between the internal side and the external side. The sample connection port comprises a first interlocking component for releasably locking the sample connection port to a cooperating second interlocking component. The internal side of the cap comprising a connection interface in fluid communication with the sample connection port. The extractor core is adapted to be removably attached to the connection interface of the top cap and has an open upstream end, an open downstream end, and an internal passage therebetween containing a substrate for collecting the biomolecules. The extractor body has a first open end configured to mate with the top cap and a second end comprising an opening configured to receive the extractor core adaptor. The extractor core adaptor has an upstream open end for mating with the downstream end of the extractor core, a downstream protrusion configured to project through the opening in the extractor body, a downstream open end, and an internal passage between the upstream open end and the downstream open end.

The system may further comprise a syringe comprising the second interlocking component adapted to connect to the first interlocking component of the sample collection port in the top cap, and a shipping container defining a volume adapted to contain the extractor core. The shipping container is adapted to releasably engage the extractor core for detaching it from the connection interface of the top cap, the shipping container further comprising a removable lid for temporarily sealing the extractor core within the shipping container.

The collection system may further comprise one or more sample processing reagent buffers such as lysing buffer, binding buffer, washing buffer and eluting buffer, or waste collection containers, one or more of these containers comprising a flexible container having an expandable volume. For example, the flexible container may be a plastic bag, which may further have one or more rigid stiffeners integrated into the bag for providing structural strength to the bag, such as rigid stiffeners that provide sufficient structure to enable the flexible container to remain in an upright position when filled or partially filled with liquid. In particular, the one or more flexible containers may comprise a sample processing container having a sealing cap and an opening in the cap sized to receive a length of tubing inserted through the sealing cap in fluid communication with an inside of the flexible container. The length of tubing inserted through the sealing cap of the flexible container may have a first end disposed inside the flexible container, and a second end comprising a first interlocking component adapted to connect to the second interlocking component of the syringe. The opening in the sealing cap may be further sized to receive the downstream end of the extractor adaptor.

The collection system may further compromise a repellent agent. Prior art processes for eluting the absorbed nucleic acids from a porous substrate require first adding a small volume of an eluting buffer on the substrate to release the bound nucleic acids from the substrate, and the collecting the elute via high-speed centrifugation or air purging. High-speed centrifugation requires an expensive centrifuge and electricity supply. Air purging may cause significant loss of sample. A method that includes first adding eluting buffer on the substrate, and then injecting a hydrophobic repellent fluid into the extractor core, causes most of the aqueous eluting buffer with released nucleic acids to be driven out from the porous substrate so that it can be easily collected.

Another aspect of the invention comprises a method for collecting a sample of biomolecules. The method comprises the steps of providing the system for collecting biomolecules as discussed herein, then collecting a volume of sample-containing fluid in the syringe, connecting the syringe to the extraction assembly via the sample collection port and connecting the downstream end of the extractor adaptor to the sealing cap of the sample processing container; and passing the volume of sample-containing fluid from the syringe through the extractor core, thereby collecting the sample on the substrate and collecting a remainder in the sample processing container. The step of passing the volume of sample-containing fluid from the syringe through the extractor core may be optionally repeated one or more times, and the method may also comprise optionally performing one or more washing steps. The method may further comprise the steps of, after collecting the sample on the substrate of the extraction core, eluting the rehydrated sample by a repellent agent; or placing the shipping container open end over the extraction core, engaging the extraction core with the shipping container, detaching the extraction core from the top cap, and temporarily sealing the shipping container with the removable lid. Thus, the system may eliminate a need for special equipment and electricity for sample processing, making it more suitable for being used at rural or remote Point Of Care (POC) settings. The shipping container may then be transported under ambient, non-climate-controlled conditions, and thereafter the method may further comprise processing the biomolecules collected in the extraction core for detection of a disease or infectious pathogens, such as deep seated infections, for example, tuberculosis, and in particular, latent tuberculosis.

BRIEF DESCRIPTION OF THE DRAWINGS

FIG. 2 depicts an exemplary filter column.

FIG. 3 depicts a cross section of the exemplary filter column/extraction core of FIG. 2.

FIG. 4 is an exploded view of the filter column of FIG. 2 and the receptacle cap of FIGS. 1A-1B showing how they interface with one another, which is identical to how the extraction core of FIGS. 9A-9B interfaces with the top cap of FIGS. 8A-8C.

FIG. 5 depicts the receptacle cap of FIGS. 1A-1B attached to an exemplary receptacle.

FIG. 6A depicts an exemplary shipping container bottom portion of the new embodiment.

FIG. 6B illustrates how the exemplary shipping container of FIG. 6A fits over the exemplary filter column or extractor core for unscrewing it from exemplary receptacle cap or top cap.

FIG. 6C is a cross sectional drawing of an exemplary shipping container top portion.

FIG. 6D is a cross sectional drawing of the exemplary shipping container bottom portion of 6A sealed by the exemplary shipping container top portion of FIG. 6C.

FIG. 6E is a perspective view of the sealed shipping container of FIG. 6D.

FIG. 7A illustrates an exemplary syringe used in an exemplary extraction system.

FIG. 7B illustrates an exemplary extractor assembly used in an exemplary extraction system.

FIGS. 7C and 7D illustrate a perspective top view and a longitudinal section view, respectively, of an exemplary sample processing/reagent-containing plastic bag for use in an exemplary extraction system.

FIGS. 9A-9C illustrate a perspective top view, a longitudinal section view, and a perspective underside view, respectively, of an exemplary extractor core.

FIGS. 12A-12C illustrate a perspective top view, a longitudinal sectional view, and a perspective underside view, respectively, of an exemplary bottom cap ring.

DETAILED DESCRIPTION OF THE INVENTION

The Systems Disclosed in the Original Applications

Figure 1A:
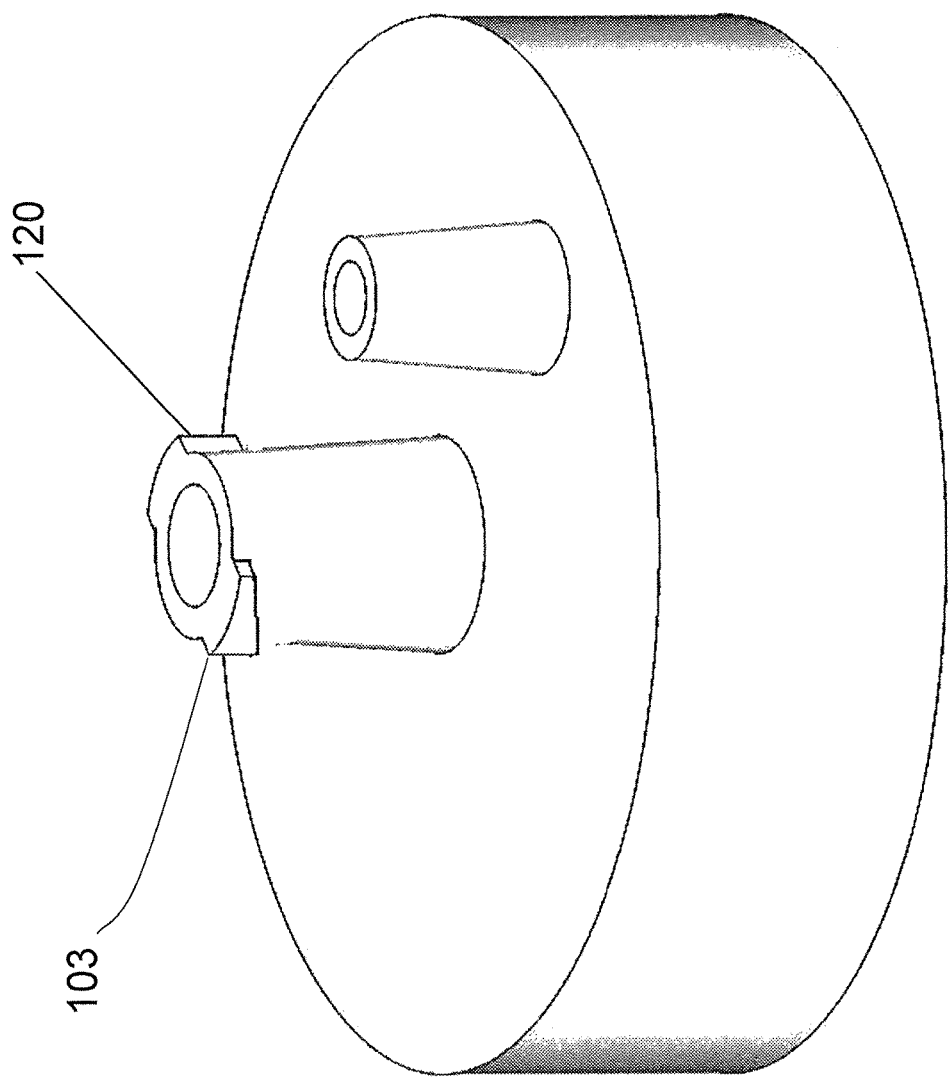
FIG. 1A depicts a perspective side view of the exemplary receptacle cap.
Figure 1B:
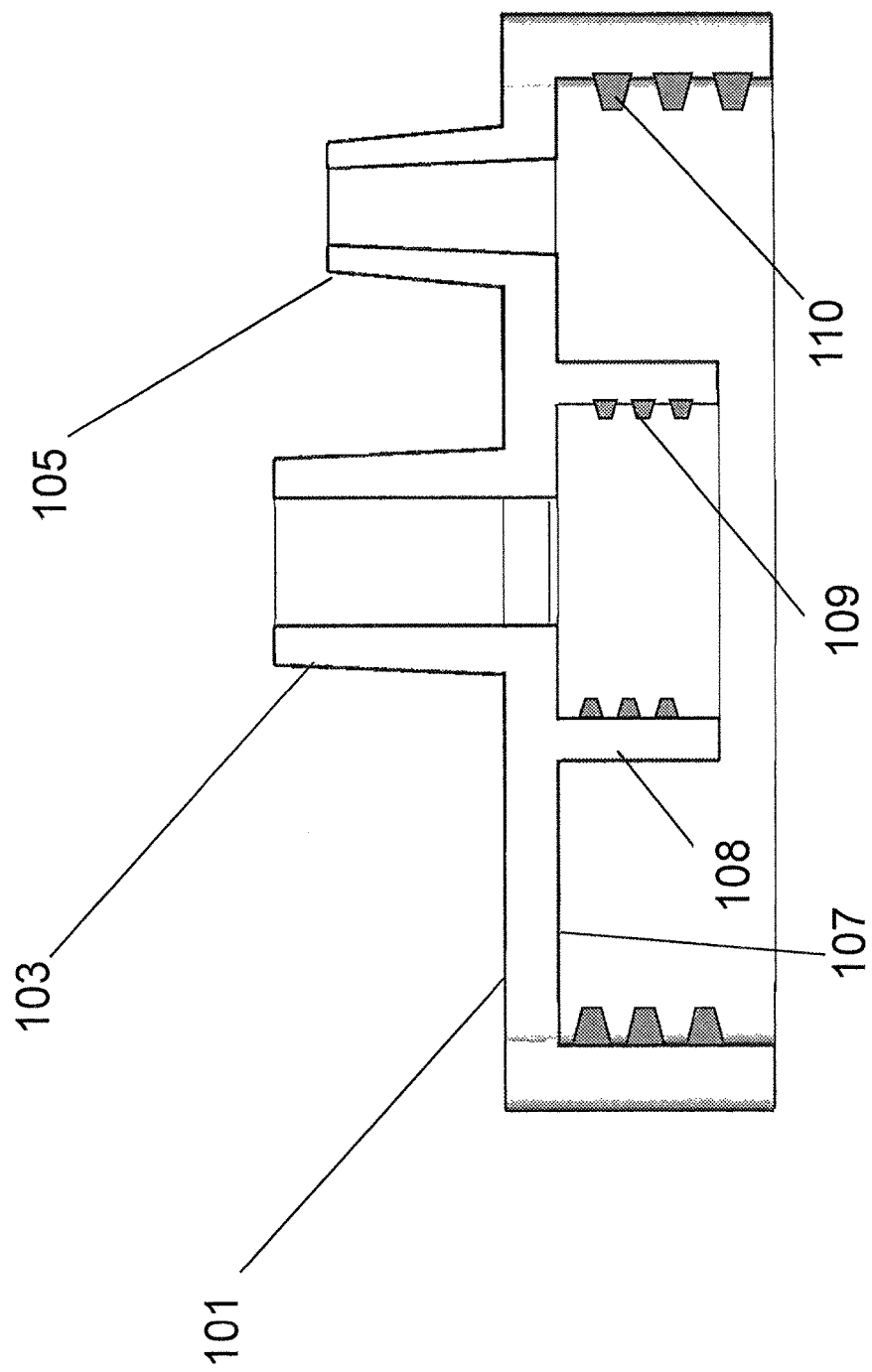
FIG. 1B depicts a cross-sectional view of the exemplary receptacle cap of FIG. 1A.

The exemplary system described in the original applications comprises a receptacle, such as receptacle 400 of FIG. 5, which defines an internal volume. Although shown with an exemplary geometry, the invention is not limited to any particular size and shape of the receptacle. As discussed herein later, in an improved embodiment, the receptacle may comprise a flexible bag, such as is shown in FIGS. 7C and 7D. The embodiment described in the Original Application has a removable cap 101, such as the exemplary embodiment depicted in FIGS. 1A-1C, having an internal side 107 facing the internal volume of the receptacle and an external side 102 facing away from the internal volume. FIG. 1A shows the external side of the cap. The cap has a breather port 105, such as a male Luer slip connection, communicating between the internal side and the external side through passageway 106, and a sample connection port 103 communicating between the internal side and the external side, through passageway 104. In the improvement over the system of the Original Application, discussed herein later, top cap 900 is essentially identical to top cap 101, but with no breather port 105. The sample connection port comprises a first interlocking component, such as a Luer lock connection 120, for releasably locking the sample connection port to a cooperating second interlocking component of a sample transfer container (not shown), such as a syringe. Both ports 120 and 105 can be easily opened or closed by Luer-fitting caps or plugs (not shown). When downward pressure is applied to the plunger of a syringe connected to port 120 to force liquid movement, port 105 is opened to allow displaced air to exit receptacle 400. When vacuum is used to force liquid movement from a connected source (which may still be a syringe), port 105 is connected to a vacuum source. The internal side of the cap comprises a connection interface 108 in fluid communication with the sample connection port 103. The cap may be threaded with female threads 110 for being screwed onto a receptacle having male threads (not shown), although any functional connection between the cap and the receptacle may be utilized. As will be discussed herein later, an improvement to the system uses flexible containers 7C and 7D with an expandable volume rather than a rigid, non-expandable container 400, which eliminates the need for breather port 105.

A filter column with a solid phase extraction matrix inside, such as a silica gel membrane, sintered porous glass frit, or glass fiber filter paper, such as the exemplary filter column 200 depicted in FIGS. 2 and 3, is adapted to be removably attached to the connection interface of the receptacle cap. For example, as shown in FIG. 1C, the connection interface 108 may have female threads 109 that mate with male threads 220 on filter column 200. The filter column has open ends 202 and 204 and an internal passage 206 there between containing a substrate 212 for collecting the nucleic acid. The filter column may also be referred to as a "hollow body" because it is designed for fluid to pass through it without the fluid being retained therein in the way that fluid is retained in a vessel or a receptacle. The filter column substrate 212 may be adjacent a porous frit 214, and a retaining ring 210 may create a frictional engagement against the inside of the column to retain the substrate and frit in a position adjacent the neck of the filter column. Extraction core 300, described in more detail herein later, may be essentially identical to filter column 200 at least with respect to the male threads that mate with the connection interface of the top cap and with respect to the substrate, frit, and retaining ring.

Substrate 212 may comprise a column binding matrix comprising a solid matrix which allows fluid to pass through the matrix. In certain aspects the matrix is highly porous so as to maximize surface area exposed to buffer solutions and thereby maximize the binding capacity of the matrix. A matrix can be made of various materials. In certain specific embodiments, the binding matrix may be a silica material (formed primarily of $SiO_2$) such as glass fiber, silica beads, silica gel, sintered porous glass frit, etc. Numerous commercial providers of silica matrix are known, such as, for example, type GF/A, GF/B, GF/C, GF/D and GF/F glass fiber filters produced by Whatman (NJ). Such filters are of particularly known for use in the purification of nucleic acid molecules. In other embodiments, a variety of solid matrices, such as ion exchange, affinity and surface modified matrices suitable for certain biomolecule extraction and separation may be applied. The binding matrix may be any material in which particles or fibers of the nucleic acid binding material may be embedded. The matrix material is generally permeable to liquids so that the sample can pass through the matrix, the nucleic acids make contact with and bind to the nucleic acid-binding material, and other components of the sample can leave the matrix. The binding matrix may comprise any support material known in the art, including materials selected from the group consisting of siliceous materials, silica gel, glass, Zeolite, aluminum oxide, titanium dioxide, Zirconium dioxide, kaolin, gelatinous silica, magnetic particles, a sintered porous glass frit, and ceramics or polymeric support materials. The nucleic acid-binding material may be any material to which nucleic acids bind (typically non-covalently) under certain conditions whereas other substances in a sample do not bind under these conditions. Nucleic acid binding is typically reversible such that the nucleic acids can be subsequently eluted again from the material by changing the conditions.

In one embodiment, column 200 may be similar in geometry to a Mobicol column, available from Boca Scientific (FL), or may be a specially modified or specially manufactured version thereof. A design with such a geometry can be centrifuged in a microcentrifuge and permits samples with large volume to be processed easily with a syringe. The porous frit 214 may comprise inert plastic with a pore size 10-90 µm. The solid extraction matrix (substrate) may comprise GF/D filter paper (Whatman, NJ), such as made by punching the filter paper into disks that fit within the inside diameter of the column. Two or more layers of the filter disks may be put on top of the frit. A back-up ring (Ring-Store, WA), such as a ring made of PTFE (such as Teflon®) or plastic such as polyethylene (PE) or polypropylene (PP), may be put on the top of the filter disks (as seen in FIG. 2) to prevent the filter disks moving. Similar internal components are present in extraction core 300.

An opener and shipping container, such as exemplary container 650 depicted in a fully assembled configuration in FIG. 6E, comprises a bottom portion 600 and mating top portion 610. The cooperating bottom portion and top portion define a volume adapted to contain the filter column for shipping. The bottom portion 600 of the shipping container has an open top and is adapted to releasably engage the filter column for detaching it from the connection interface of the receptacle cap. For example, the filter column may have a tab 222 shown in FIG. 2 or 362 shown in FIG. 6B, or extraction core 300 may have a tab 360 as shown in FIG. 9C, any of which are configured to be engaged by notch 602 of FIG. 6A. The enclosed shipping container is sealed from the environment to prevent contamination and moisture which may cause accelerated degradation (hydrolysis) of nucleic acid, in particular RNA. The enclosed shipping container may further comprise a pre-packaged desiccant that induces or sustains a state of dryness (desiccation), such as granular or beaded form of silica gel, therein, such as desiccant 612 depicted in the upper portion of the container in FIGS. 6C and 6D. The desiccant location could also be in a lower portion of the container and is not limited to any specific location or configuration. The desiccant may comprise any suitable material known in the art for providing and sustaining desiccation, such as but not limited to, montmorillonite clay, lithium chloride, activated alumina, alkali alumino-silicate, DQ11 Briquettes, silica gel, molecular sieve, calcium sulfate, or calcium oxide. The desiccant may contain a moisture indicator that gradually changes its color when it transitions from an anhydrous (dry) to a hydrated (wet) state, such as is known for some silica gels.

Although shown with the sample connection port protruding from the external side of the cap with a Luer lock fitting, the invention is not limited to any particular type of interlocking connection, nor to any particular configuration of the sample connection port. While some type of locking engagement between the sample connection port and the sample container is preferred, any type of reversibly locking engagement may be provided. The sample transfer container is not shown, but may be a standard syringe with a cooperating Luer lock fitting. In an exemplary method, therefore, the syringe is interlocked with the receptacle cap, and the syringe plunger is depressed to force a solution containing nucleic acid, in the presence of binding reagents such as chaotropic reagents and alcohol, to be passed through the filter column. The nucleic acid is thus retained on the filter 212, while the filtrate passes into the receptacle 400. As noted above, in the embodiment with a rigid receptacle 400 and a breather port 105, the syringe plunger may be depressed manually with port 105 open, or a vacuum source may be attached to port 105 such that the vacuum causes the syringe plunger to be depressed as the solution empties from the syringe.

Chaotropic reagents are well known in the art as substances that change the secondary, tertiary and/or quaternary structure of proteins or nucleic acids but do not affect at least their primary structure. Examples are guanidinium thiocyanate, guanidinium hydrochloride, NaI, KI, sodium thiocyanate or combinations of these substances. Chaotropic reagents disturb the ordered structure of liquid water and cause DNA or RNA to bind from this aqueous solution to a glass surface. Under some conditions, inclusion of alcohol, such as ethanol or isopropyl alcohol, facilitates NA binding to the surface. Substances such as NaCl, KCl or CaCl2 may be present in the solution in order to modify the ionic strength. The property of DNA and RNA to bind under chaotropic conditions to glass surfaces is used to isolate them from a solution containing other biological materials. After the binding step, washing and cleaning buffers may be applied to remove contaminants. Binding to the glass surface is reversible, as, for example, if the concentration of the chaotropic reagents is reduced or the chaotropic reagents are entirely removed, the DNA or RNA can be eluted again. An eluting buffer may be pure DNase/RNase-free water or a buffer containing low concentrations of Tris (hydroxymethyl)-aminomethane and EDTA (ethylenediaminetetraacetic acid), typically, at 5-10 mM and 50-100 µM, respectively. Commonly, the volume of eluting buffer (EB) is in the range of 50-200 µl.

Prior art methods typically collect elute from a filter column using high-speed centrifugation. In order to recover the elute from porous matrix as much as possible, a high-speed centrifuge, i.e., having a relative centrifugal force (RCF) >10,000 g, is often required. Alternatively, repeated air purging may be adopted in some cases, however, only a portion of the aqueous solution is recovered. In one collection method embodiment of the present invention, a hydrophobic repellent is adopted to collect the elute manually without the requirement of electricity and equipment. Suitable hydrophobic repellent agents preferably have the following characteristics: high hydrophobicity, low viscosity, low specific density (i.e. <1, lower than the density of water), low surface tension and high spreadability, immiscible with aqueous phase, non-volatile, compatible with common plastics (or at least with the plastics used in the system described herein), chemically inert, and non-toxic. Surprisingly, a group of polydimethylsiloxanes (PDMS, silicone oil, or silicone fluid) have been found that meet all of these requirements. The viscosity of polydimethylsiloxane is dependent its polymerization, i.e., the lower the polymerization, the lower viscosity. PDMS are excellent repellent agents.

In an exemplary method, when the parts of 101 and 200 are assembled and connected as indicated in FIG. 4, or when the parts 410, 500, 900, and 800 of extraction assembly 10 are assembled as shown in FIG. 7B, after sample collection, a small volume of eluting buffer, e.g., 50-200 µl, is added on the porous substrate through the port 103, and the aqueous EB is absorbed quickly into the porous matrix. After that, a volume of PDMS, e.g., 0.2 to 1 ml, is injected vertically by a syringe connected tightly to port 103. Hydrophobic PDMS has less density than aqueous EB. Therefore, in the process of slow injection, aqueous EB, including trace amount attached to the surface of the porous matrix, is displaced by the PDMS and eluted out from the outlet 204 by gravity. Furthermore, a needle may attached to outlet 204 so that the elute may be more precisely collected. The hydrophobic PDMS forces the aqueous elute to form a single piece under the bottom of a collection tube, separated by a clear boundary with an upper layer of PDMS, because of its very low surface tension. Suitable low viscosity PDMS includes PSF-5, 10 and 20 cSt Pure Silicone Fluids, supplied by Clearco Products Co., Inc. (PA).

The Original Applications disclose a collection system embodiment further comprising a vacuum chamber (not shown). The improvements of the new embodiments described herein avoid the need for a vacuum chamber and a breather port on the top cap, thereby minimizing the overall amount of equipment needed to process the sample.

New Embodiment Additional Details

An exemplary biomolecule extractor of the present invention is used for enriching and extracting biomolecules from large volumes of fluids containing biological molecules, particularly, macromolecules such as nucleic acids, proteins lipids, polysaccharides. The extraction is based on solid phase extraction (SPE). In general, SPE comprises a mobile system (liquid phase) with targeted biomolecules and a stationary phase (solid phase) including a surface comprising functional groups with high affinity to the targeted molecules. In an typical process, the liquid phase, driven by positive or negative pressures, or simply by gravity, passes through a porous solid matrix comprising the surface with the functional groups, and the targeted biomolecules absorb or bind to the functional groups, often reversibly, and are eluted from the matrix in a subsequent step.

The exemplary extractor device system has the following features: 1) an enclosed system essentially contamination-free; 2) configured for portable and manual operation of the extraction processing, including a capability to be operated instrument-free and electricity free operation; 3) configured to allow large volume of biologic fluids, for example, 1-5 ml, to be processed and enriched up to 100 fold for low abundance molecules, such as cell-free circulating nucleic acids of fragmented DNA and RNA of cancers, pathogens like TB (tubercle bacillus), and fetal DNA, in plasma, serum and other body fluids; 4) configured to stabilize molecules, such nucleic acids, particularly RNA species, to enable sample transportation at ambient conditions; 5) configured to elute the extracted nucleic acids without centrifugation; 6) configured for pathogen-free processing of the sample in the device to prepare the sample for down-stream applications, in the cases of nucleic acids, for example, PCR, quantitative PCR (qPCR), digital PCR (dPCR), microarrays and next generation sequencing NGS).

An exemplary extraction system, as depicted in FIGS. 7A-7D comprises an extractor assembly 10 (FIG. 7B), preferably plastic, a set of multiple sample processing/reagent-containing bags (FIGS. 7C, 7D), preferably plastic, and a protection container for extraction core detaching and transportation (FIGS. 6A-6F as discussed in detail above). The system is further adapted for use with, or may comprise, one or more syringes for its operation (FIG. 7A).

Figure 8C:
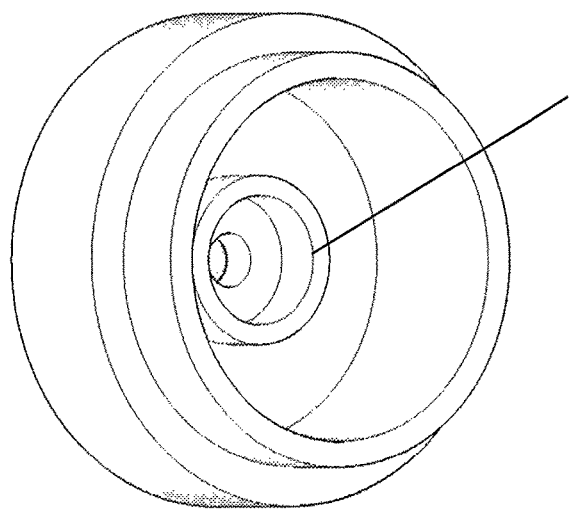
FIGS. 8A-8C illustrate a perspective top view, a side view, and a perspective underside view, respectively, of an exemplary top cap of the exemplary extractor assembly.
Figure 8B:
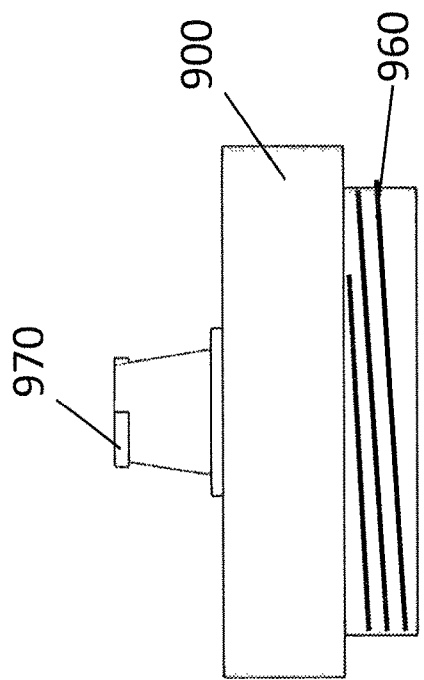
Figure 8A:
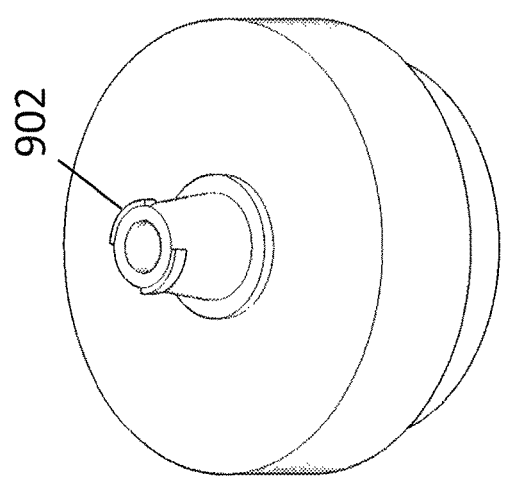

The exemplary extractor assembly 10 has five components: (1) a top-cap 900 (FIGS. 8A-8C); (2) an extraction core 300 (FIGS. 9A-9C) (essentially the same as the "filter column" referred to in the disclosure of the Original Applications); (3) an extraction core adaptor 410 (FIGS. 10A-10C) extending from the extraction core; (4) an extractor body 500 (FIGS. 11A-11C); and (5) a bottom cap ring 800 (FIGS. 12A-12C). The top-cap, as depicted in FIGS. 8A-8C, has a locking connector 902 (such as a female Luer lock connector) on its outside top, which is adapted to be connected to a plastic disposable syringe. The top-cap 900 is further configured to detachably receive the extraction core 300 (such as with a screw connection) on an extraction core receiving member 910 disposed on the inside of the top-cap. Top cap 900 is essentially identical to removable cap 101 illustrated in FIGS. 1A-1C and described in the Original applications, except that top-cap 900 has no breather port and no other openings in the cap providing communication between the interior and exterior surface of the cap other than sample port 902. Thus, top-cap 900 is generally identical in longitudinal section to cap 101 in FIG. 1B, except there is no breather port 105.

The extraction core, as depicted in FIGS. 9A-9C, has two connectors: an upstream connector 310 for connection to the receiving member 910 of top-cap 900 so that extraction core is in fluid communication with the channel defined by female locking connector 902 on the top-cap, and a downstream connector 320 (such as a Luer slip male connector) configured for connection to the adaptor 410. The extraction core 300 comprises a fixed porous solid absorbent matrix 340 inside. As shown in FIG. 9B, in one embodiment, back-up ring 330 disposes absorbent matrix 340 on top of a porous frit 350. The outer surface of extraction core has one or more members, such as tabs 360 and slots 364 interposed between the tabs, for meshing with a mating set of tabs and slots to provide a mechanism for receiving torque applied to rotate extraction core 300 to detach it from the receiving member 910 in top-cap 900. For example, as shown in the schematic embodiment shown in FIGS. 6A and 6B, protection container 600 has a single slot 602 for receiving tab 362 on extraction core 300. It will be understood that rather than a single tab and mating slot, each of the protection container 600 and the extraction core 300 may have a plurality of intermeshing tabs and slots that designed to mesh together, such as the plurality of evenly spaced tabs 360 depicted in FIGS. 9A and 9C.

Figure 10C:
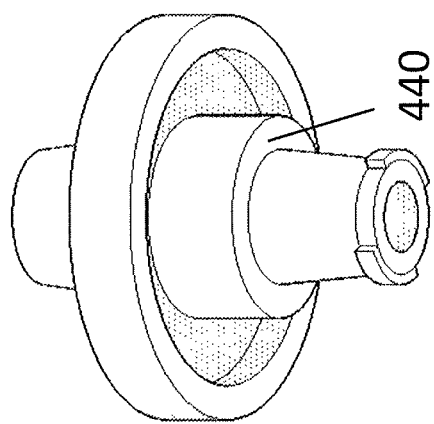
FIGS. 10A-10C illustrate a perspective top view, a side view, and a perspective underside view, respectively, of an exemplary extraction core adaptor.
Figure 10B:
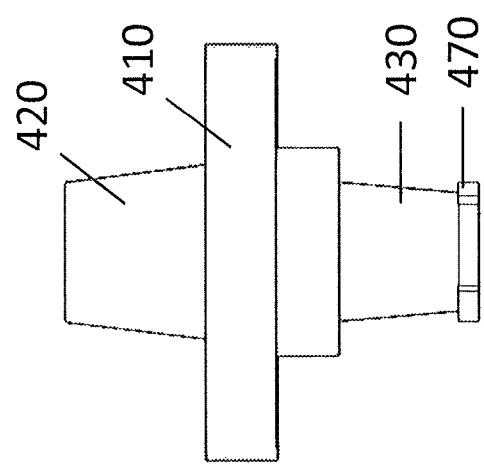
Figure 10A:
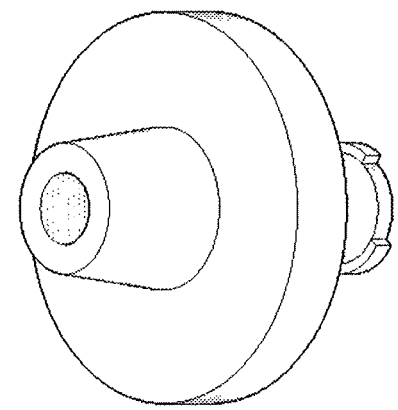
Figure 11C:
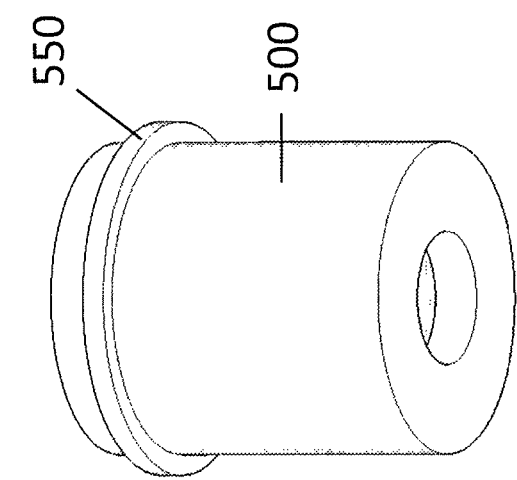
FIGS. 11A-11C illustrate a perspective top view, a side view, and a perspective underside view, respectively, of an exemplary extractor body.
Figure 11B:
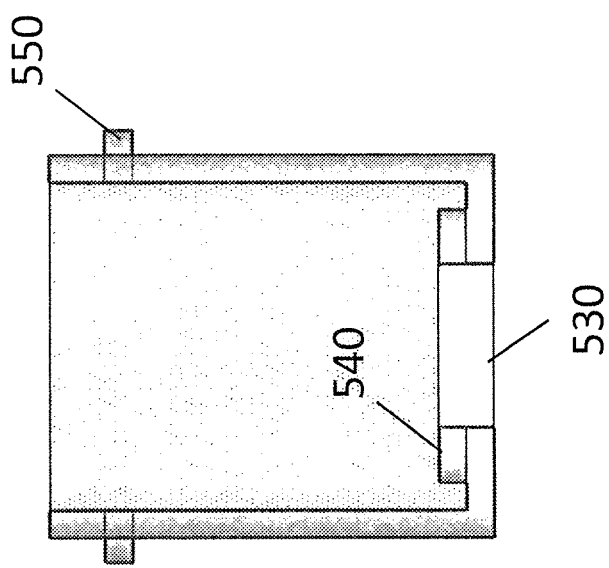
Figure 11A:
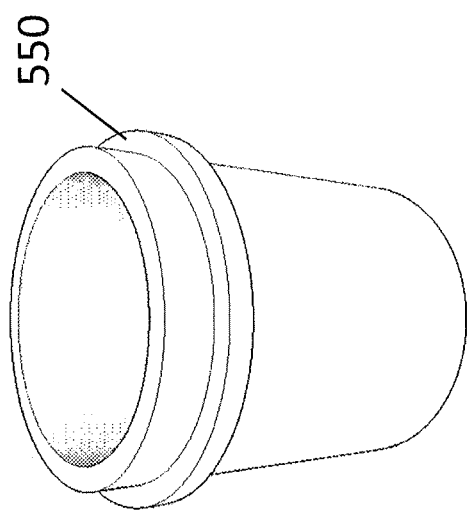

The adaptor 410, as depicted in FIGS. 10A-10C, is adapted to operate as an extension of the extraction core when its upstream connector (such as a Luer slip female connector 420) is attached to the downstream connector 320 of the extraction core. The adaptor further comprises an extended downstream connector 430, such as an extended Luer lock female connector extending away from the extractor body. The extractor body 500, as depicted in FIGS. 11A-11C, is a tube-like container. When extraction core 300 is firmly attached to the inside 910 of the top-cap 900, with the adaptor 410 attached to a downstream connector 320 of the extractor 300, the assembled components set is configured for insertion into and mating with the extractor body 500, with the adaptor extended downstream connector 430 (i.e. the Luer lock female end) extending through the bottom hole 530 of the extractor body such that connector 430 extends outside of extractor body 500, as shown in FIG. 7B. The inside bottom of the extractor body features a circular ridge 540, which mates with a circular ridge 440 on the adaptor bottom.

Alternatively, with minor modifications, a Luer lock male connector can replace the Luer lock female end of the adaptor 410. The invention is not limited to Luer lock connectors or to male or female connectors in the locations indicated. In each case, other types of connectors may be used, and those of skill in the art can appreciate that the male and female connectors can be substituted for one another throughout, with minor modifications. In some embodiments, the inside circular ridge of the bottom of extractor body and the circular ridge of the adaptor bottom can have one or more members, such as for example mating flange(s), dent(s), and/or protrusion(s), opposite each other that prevent rotational movement of the adapter relative to the extractor body when engaged (not shown on FIG. 10A-10C or 11A-11C). On the wall of the outside of the extractor body, a circular ridge 550 may serve as a stop for engagement of the extractor body with the top cap and bottom cap ring as further described below. The bottom cap ring, as depicted in FIGS. 12A-12C, comprises a female screw fitting on its inside wall, and is adapted to be passed over the extractor body from the bottom, to engage the ridge 550 on the outside wall of the extractor body with an inner surface 850 of the cap ring 800, and to engage the male screw flights 960 of the top-cap with its female screw fittings 860, to minimize or eliminate liquid leaks when the whole assembly as described herein is firmly connected together and the extraction is in process.

A set of sample processing/reagent/waste collection containers may be further provided, as depicted in FIGS. 7C and 7D. The bags contain different reagents, e.g. Lysing Buffer (LB), Binding Buffer (BB), Washing Buffer (WB), Cleaning Buffer (CB), eluting buffer (EB) and repellent fluid (RF) as further described herein. The capacity of the containers may vary, from 50 ml down to 2 ml, depending upon the amount of reagent needed for operations. The containers are typically flexible, such as bags made from Poly Ethylene (PE), Poly Propylene (PP), Poly Vinyl Chloride (PVC), and/or Ethyl Vinyl Acetate (EVA). A representative reagent/sample processing container is exemplified by LB bag (FIGS. 7C and 7D). The LB bag has approximately 50 ml capacity and has a round columnar shape. The inside wall of the bag contains four rigid ridges 706, which help provide more structure to enable the flexible bag to remain in a straight standing position when processing the sample. The exemplary bag has a round sealing cap 702 with a tubing channel 704 on the cap, such that tubing 708 can be inserted in fluid communication with the inside of the bag. The other end of the tubing may comprise a connector (not shown), such as a Luer lock female connector, which can be directly connected to syringe (such as a Luer lock syringe), to receive a liquid specimen, such as plasma, serum, or other biological fluids by syringe injection. The LB bag contains preloaded lysing buffer. The biological fluid is mixed with the lysing buffer in the bag, and may be also incubated, in a water bath or a heat block, to accelerate nucleic acid release from other biological complexes. The round shape of the LB bag is fitted into commonly used 50 ml centrifuge tube racks, or heat blocks. Upon completion of a lysis process, binding buffer is transferred from the BB bag to the LB bag, though a syringe drawing from the BB bag and injecting into the LB bag. After mixing by repeated syringe drawing and injecting from the LB bag, the lysate and binding buffer mix is drawn into the syringe, and the syringe is then connected to the (e.g. Luer lock female) connector 970 on the top of the top cap 900 of the extractor assembly 10, and the Luer lock female connector of the bottom of the extractor assembly (i.e. the downstream connector 470 of the adaptor 410), is then connected to the LB bag, such as, for example, through a Luer lock male-male adaptor (not shown). By depressing the syringe plunger, the mix is injected into the extractor, passing through the solid absorbent matrix, with any uncaptured liquid flowing back into the LB bag. The targeted molecules, in those cases, fragmented short DNA or RNA, are absorbed on the surface of the solid matrix.

Use of bags or other flexible-volume containers for the collection containers provides certain advantages, including the ability to use a non-vented cap on the collection system. Because the bags have a flexible volume, sufficient volume can be reserved in the bags to accommodate small amounts of air (e.g. 1-5 ml) intentionally introduced in the syringe to follow each volume of liquid passed through the extractor. This small amount of air is helpful for driving air from the residual liquid in the porous matrix after the liquid in the syringe has been first discharged. Thus, the collection bags or other flexible volume containers may be designed with a sufficient amount of reserved volume to accommodate not just any expected amount of liquid to be added to the bag during processing, but also any expected amount of additional air introduced during the expected number of syringe introduction steps during overall processing. In addition, flexible volume containers allow for a connected syringe-extractor-container system in which the three parts (syringe, extractor, and flexible volume container) form an enclosed connection without communication with the environment. When the syringe pushes or draws liquid into or from the flexible container, the volume of the flexible container is changed, without a need to dispense liquid or air outside of the enclosed system or to draw outside air into the enclosed system. Thus, this closed system arrangement better minimizes or prevents contamination as compared to an open system. The system also allows liquids to flow bi-directionally so the extraction process may be repeated multiple times to achieve maximum efficiency.

Though control of the flow rate, and, through repeatedly drawing and injecting several times (2-10 times), the targeted molecules have multiple chances of interacting with the absorbent matrix, maximizing recovery of short nucleic acids from the large volume of the lysate. After completion of the extraction process, the LB bag is detached from the extraction assembly (such as from the optional Luer lock male-male adaptor). The adaptor on the extraction assembly is connected to washing buffer bag and cleaning buffer bag sequentially, repeating the drawing and injecting with a smaller new syringe (the volume of washing and cleaning buffers are much smaller then specimen and—binding-lysing buffer mixture, approximately a few milliliters). Again, repeatedly drawing and injecting the washing buffer and cleaning buffer through the extractor may help more efficiently remove contaminants from the absorbent matrix, to minimize the potential of such various contaminants from significantly affecting downstream applications.

Upon the accomplishment of the extracting, washing and cleaning, the extraction core is ready to be removed from the extractor assembly via the following steps: (1) detaching the Luer lock male-male adaptor from extended connector 470 protruding from extraction assembly 10; (2) unscrewing the bottom cap ring 800; (3) removing the top-cap 900 from the extractor body 500; (4a) detaching the extraction core 300 from top cap 900 receiving member 910 with the protection container 600 and sealing the protection container (as described in more detail in the Original Applications) with lid 610; (4b) alternatively, adding eluting buffer by pipetting and then injecting repellent fluid (RF) though the inlet port of top cap 900 for immediate elution. Thus, the extraction core with extracted nucleic acids on its absorbent matrix is ready for immediate performance of elution steps in downstream applications, or to be stored or ambient transportation.

The method comprising treatment with repellent fluid as describe herein may be used for recovering biomolecules from any type of substrate in any type of filtration or collection system, not limited to the systems described herein, although it should be understood that the method may be particularly useful for use in connection with any of the systems described herein, including those disclosed in the Original Applications as well as the New Embodiments.

The extraction core may be preferably configured to accommodate a commonly used 96-well format, so that the elution step can be accomplished in high-through-put processing.

The extraction core contains a plastic porous frit, a layer of absorbent matrix, and a plastic back-up ring, or another plastic porous frit. The plastic frit and the plastic back-up ring is used to fix the absorbent matrix to its position in the extraction core and allow liquids flow through the absorbent matrix, as further described with respect to the system disclosed in the Original Applications.

Furthermore, extraction core 300 is essentially identical to filter column 200 with respect to its filtration components and with respect to its upper portion that interfaces with the receptacle cap 101/top cap 900, but extraction core has a downstream connector 320 that is longer than the open end 204 of filter column 200, and extraction core 300 as a whole is sized to fit within extraction assembly body 500 and to interface with adaptor 410. Whereas the internal filter components are located near the downstream end of filter column 200, the internal filter components are located longitudinally approximately in the middle of extraction core 300, to provide space for the elongated downstream connector to interface with adaptor 410 and the downstream end 430 of adaptor 410 to protrude through opening 530 in extraction body 500. The extraction core and filtration column are not limited to any particular sizes, shapes, or other geometry, however.

With respect to all of the components described herein, it should be understood that interface features such as locking fittings or threads are depicted only in certain figures for emphasis, and may not be depicted in others, for simplicity. Furthermore, although certain exemplary types of interface features are described herein with respect to certain components, it should be understood that the invention is not limited to the specific types of interface features discussed, nor limited to the presence or absence of interface features with respect to specific components. Accordingly, components having certain interface features depicted may be provided with other types of interface features or no interface features at all, and other components depicted without interface features, may have any type of interface feature known in the art.

Additional Features
Absorbent Matrix

Absorbent materials and pore size vs. flow-rate has been considered and tested. Several absorbent matrices are available, including silica membranes, glass fiber papers, and sintered porous glass frit. In general, the large surface area of those silica materials provides sufficient binding (absorption) sites (up to 100 μg NA). The small amount of cfNA (often less than 100 μg) is unlikely to saturate the binding surface; however, the binding surface may have an effect on the absorption rate of cfNA, causing uncompleted extraction or un-tolerated flow rate or even high pressure. Increased pore size of the absorbent matrix is correlated negatively with surface area and positively with flow rate. A porous glass frit with 10-50 μm pore size provide good fluid flow as well strong binding to short nucleic acids. Its fast flow rate allows sample repeated passing through it, thus significantly increasing the extraction efficiency. In addition, pre-treatment of the surface of absorbents may enhance the extraction of cfNA.

Size Selective Extraction

It is well known that tumor-derived or fetal-originated cfDNA are generally more fragmented, i.e., shorter, than the cfDNA from normal tissues and from maternal origination. The genomic DNA released from blood cells during specimen collection, storage/transportation, and processing significantly affect cfDNA population and consequently the detection sensitivity for targeted cfNA. However, selective removal of long DNA from body fluids prior to cfNA extraction is possible. By using weak anion exchange magnetic beads long DNA (>1000 bp) was successfully removed from urine, which significantly increased the portion of fragmented cfDNA in the final extracts. Others also have reported extraction gDNA from blood with an anion exchange matrix. Thus, an additional extractor as described herein containing anion exchange matrix, may be used for removing the majority of long DNA before cfNA extraction under certain compatible conditions. Functional anion exchange matrices, such as carboxylated or DEAE-conjugated beads, resins, and/or filter papers are available on the market for performing this step.

Thus, the additional extractor can be made with different matrix and different reagent system. For example, in order to remove large size cellular DNA from body fluid, an anion exchange extractor can be constructed as follows, with reference to FIGS. 9A-9C: after placing a plastic porous frit 350 into extraction core 300, 200 μl of DEAE Sephadex A-50 beads (GE Healthcare Life Science) in buffer suspension (50%) is loaded on the first frit in the place of absorbent matrix 340, and a second frit is placed on the top of DEAE Sephadex bead layer in place of ring 330, thereby fixing the beads between the two frits. The remaining components of the extraction system are assembled as described previously. pH buffer and salt are preferably first added to the body fluid lysate, to establish desired pH and salt conditions (known in the art) at which large DNA in the lysate will tightly bind to the beads, but small DNA will not. Thus, the fluid that passes through the extractor as configured above and collected into the collection bag will have fewer large size cellular DNA molecules than prior to such extraction. In the collection bag, the fluid is then mixed with additional binding buffer and passed through a second extractor having the silica matrix as described above. The binding buffer is now conditionalized for small DNA. Thus, a suitable kit for such a process may comprise a first extractor configured with a first matrix for removing large size cellular DNA, and a second extractor configured with a second matrix for retaining the desired sample of biomolecules for shipping and analysis.

Sample Collection

Consistent with the lysing container described in the Original Applications, generally, the LB bag may contain pre-formulated lysis reagents, which may comprise, for example, at least: a nonionic detergent such as Triton X-100 or BJ58, or a combination of the nonionic detergent with an anionic detergent, such as sodium lauroyl sarcosinate, a protease such as proteinase K, a salt or chaotropic agent, such as Lithium chloride, guanidine, guanidine thoicyanate, urea, a reducing agent such as Dithiothreitol (OTT), a chelator such as ethylene diamine tetraacetic acid (EDTA), and a buffer such as tris(hydroxymethyl)aminomethane (Tris). It is well-known guanidine and guanidine thiocyanate have strong DNase and RNase inhibitory activity at molar concentration. The lysing reagents may in a solution, or in a dried form (dehydrated), for example, by lyophilization (freeze-drying) or spray-coating within the lysing container.

The specimens, in the forms of aqueous fluids, such as blood, plasma, serum, sputum, saliva, urine, Cerebrospinal fluid (CSF), pleural effusion, peritoneal fluid, synovial fluid, etc., may be directly, or with additional water, added into the LB. When the aqueous fluid is added into LB, the sample fluid mixes with lysing solution, or re-hydrates the dried lysing reagents, to form a complete sample-lysing buffer mix. Preferred specimens are plasma or serum, and the preferred volumes of plasma or serum collected are in the range of 1-20 ml, more preferably at least 2 ml, even more preferably 2-10 ml, and most preferably 2-5 ml.

Other specimens in high viscosity form, or in semi-solid and solid forms, such as pus, cell suspensions and tissues, may be added into the LB with additional water in an amount as needed to re-hydrate the dried lysing reagents, to maintain an optimal ratio of the sample volume to the lysing solution.

In a preferred embodiment, after the extraction, the collected sample may be further processed by washing and rinsing, as described above and in the Original Applications, and in any way known in the art.

Although shown with a tab on the filter column and a mating notch on the shipping container, any member disposed on the filter column adapted to be releasably engaged by a cooperating second member disposed on the shipping container, and capable of transmitting sufficient force to the filter column to unscrew it from its threaded connection with the receptacle cap, may be provided. Similarly, although shown with a threaded connection between the filter column and the receptacle cap, any type of interlocking connection may be used, and the respective elements of such a system may utilize any type of cooperation between the shipping container and the filter column to detach the filter column from the cap in a preferably sterile manner.

The filter columns may be sized to fit within a sample holder (not shown) for receiving a plurality of filter columns and adapted to fit in a centrifuge for centrifuging the plurality of filter columns together at one time, such as but not limited to a size accommodated to fit a 96-well format for semi-automatic or full-automatic processing and handling.

The collection system may be sold as part of a kit comprising one or more of the materials required to perform a particular type of test, such as but not limited to the following: means for extracting a fluid sample from a patient (such as a needle and syringe for pulling blood, serum, plasma or other body fluids), sample processing/reagent/waste collection containers, including containers containing reagents (e.g. Lysing Buffer (LB), Binding Buffer (BB), Washing Buffer (WB) and Cleaning Buffer (CB), Elution Buffer (EB) and Repellent Fluid (RF)) as further described herein, sample transfer means (such as a syringe), the extractor assembly as discussed herein, and the shipping container as discussed herein.

In other embodiments, the various parts above may be sold separately. Ideally, for most types of testing, and in particular for the tuberculosis detection method referred to herein, all of the parts that touch the sample or sample containing fluid from the time it is extracted from the patient until the nucleic acid is deposited on the substrate in the filter column, should be sterile or not contaminated by nucleic acid from any other sources, for example, from the operator or from environment, and not be contaminated by universally existing DNases and RNases, which quickly degrade nucleic acid. Various containers, syringes, and receptacles as discussed herein may be standard components well known in the laboratory/healthcare fields. The innovative receptacle cap, however, with connected filter column, is specialized for this particular collection system.

Thus, another aspect of the improvement may comprise a sterile removable cap for a receptacle, the cap having an internal side for facing the internal volume of the receptacle and an external side opposite the internal side, the cap comprising no breather port communicating between the internal side and the external side, and a sample connection port communicating between the internal side and the external side, the sample connection port comprising a first interlocking component for releasably locking the sample connection port to cooperating second interlocking component, the internal side of the cap comprising a connection interface in fluid communication with the sample connection port. The removable cap described above may be sold separately, or in another embodiment, complete with a sterile filter column as discussed herein, removably attached to the connection interface of the receptacle cap.

All the parts of the system described herein may be made by any method known in the art, such as by thermoplastic injection molding. Preferred thermoplastics include polyethylene (PE), polypropylene (PP) and polyethylene terephthalate (PET), but the invention is not limited to any particular material or method of construction.

An exemplary method for using the system discussed herein may be performed as follows.

(a) collecting a volume of sample-containing fluid, which may be treated and incubated with a lysis buffer and binding buffer with chaotropic agents, salts and precipitant such as alcohol, in the LB bag to release nucleic acids from complexes, cells or other particles in a biological sample, and extracting the crude lysate from the LB bag using a syringe;

(b) connecting the syringe containing the crude lysate to the upstream end of the extractor assembly and the LB bag to the downstream end of the extractor assembly;

(c) passing the volume of sample-containing fluid from the syringe through the extractor assembly, thereby collecting nucleic acid from the crude lysate sample on the substrate and collecting a remainder in the LB bag;

(d) washing the nucleic acid bound filter matrix in the column with washing buffers;

(e) dehydrating (and also simultaneously further washing and desalting) the nucleic acid bound matrix by passing a volume of solvent though the column, preferred with 100% ethanol or acetone;

(f) placing the shipping container bottom portion over the filter column, engaging the filter column with the shipping container, and detaching the filter column from the receptacle cap;

(g) temporarily sealing the shipping container by mating the shipping container top portion and shipping container bottom portion, the sealed shipping container preferably containing a pocket of moisture absorbent (desiccant), such as granular or beads silica gel.

(h) alternatively, instead of conducting steps (f) and (g), without detaching the filter column, instead, directly adding EB and then injecting RF by a syringe through the inlet on the top cap 200, to collect elute immediately in another container;

(i) shipping the container of elute for processing, or processing it immediately.

Unlike DNA molecules, which are relatively stable, RNA molecules are more susceptible to degradation due to the ability of the 2' hydroxyl groups adjacent to the phosphodiester linkages in RNA to act as intramolecular nucleophiles in both base- and enzyme-catalyzed hydrolysis.

Washing step (d) may comprise treating the collected sample on the substrate by passing one or more volumes of treatment fluid through the filter column. For example, the treatment may comprise stabilizing the sample of nucleic acid for shipment, such as washing the sample with a washing fluid, such as a fluid comprising ethanol. In one embodiment in which the sample transfer container comprises a syringe, the method of passing the volume through the filter column comprises manually applying pressure to a plunger of the syringe. When ready for a downstream nucleic acid assay, the nucleic acid bound on the substrate in the filer column is released and eluted out from the filter column, such as by adding a small amount of elution buffer or pure water to the filter (solid matrix) to release bound nucleic acid and collecting the elute in another small container by applying air pressure or centrifugation as is known in the art, or more preferably by applying fluid pressure (injecting RF) through the column as described herein. After using the fluid pressure technique described herein, the filter column may still be air purged or centrifuged, if desired, for additional collection.

While not being limited to any particular use, the aforementioned collection system may be particularly useful in connection with a method for detection of infectious pathogens, such as tuberculosis, as outlined herein below. The system and method may be particularly useful, however, in connection with any method that uses collection of cfNA for diagnosis, such as methods for early diagnosis of fetus genetic disorders, tumor diagnosis and infections in deep tissues, like LTBI. In summary, the system and method may be particularly useful in connection with any methods based on evaluation of NA material that contains alterations in NA information distinguishable from the host body. The system and methods described herein are particularly useful in fields in which extraction and preservation is important. Detecting low concentrations of cfNA in blood requires a relatively large volume sample (2-5-10 ml), because when reagents are added, the total volume easily reaches 20-50 ml, which is difficult volume to handle or automate using previously existing processes. RNA presents problems due to its stability. Accordingly, the method and system is particularly well suited for processes relying on detection of low concentrations of cfNA, specifically RNA, in bodily fluids.

EXAMPLES

Example 1—Construction of MOE Device

A prototype of the filter column 200 as depicted in FIGS. 2-4 was constructed. A suitable sized absorption matrix disc 212 was punched from GF/D fiber glass filter paper (Whatman, NJ) and inserted on the top of the inert PP porous filter 214, then a PP backup ring 216 was tightly placed on the top of absorption matrix disc 212, to fix the assembly. A cap 101 with a Luer-Lock connection on its top was screwed and sealed on the filter column. The cap with assembled filter column was then screwed and sealed into an empty 50 ml plastic disposable centrifuge tube. The whole device as described above is referred to further herein as an MOE (Manually Operated Extraction) Device 400. Multiple MOE filter devices used in the following examples may be constructed in the same way.

Example 2

Preparation of human pooled plasma: Fresh drawn blood from 10 healthy donors was centrifuged at 4000 G for 20 minutes. Plasma fraction was removed from each blood collection tube and pooled together in a 50 ml centrifuge tube. The pooled plasma was vortexed and frozen at −20° C.

Example 3

Extraction of cfDNA from pooled plasma: In this example, only the MOE filter column was used with following buffers and protocol:
Buffers: Lysis Buffer (LB): containing guanidine thiocyanate (GITC), detergent Triton X-100, Proteinase K and EDTA.
Binding Buffer (BB): containing GITC and isopropanol (IPA), mixing very well.
Washing Buffer (WB): containing Tris, EDTA, salt, ethanol, pH 7.0.
Elution Buffer (EB): containing Tris and EDTA, pH 7.5.
Protocol:
1. Lysis: Draw 2 ml of defrosted pooled plasma by a 10 ml syringe with a long needle, into a 50 ml plastic centrifuge tube containing 2 ml LB, mix well by vortexing, incubate in 60° C. heat block for 30 minutes. Cool down at room temperature.
2. Binding: Draw 16 ml of BB into the sample lysate tube, mix it by vortexing, keep it in room temperature for 10 minutes.
3. Binding and Extraction: Draw all the content in the 50 ml lysate tube into a 30 ml Luer-lock syringe with a long needle, continuing until drawing about 5 ml air into the syringe, screw the Luer-lock syringe onto the female Luer-lock connector on the cap of assembled MOE device 400, which is seated in a rack firmly. Press the syringe plunger down until all liquid and air in the syringe pass through the filter column. The waste is collected in the 50 ml tube of the MOE device. This procedure may take 1-2 minutes. Unscrew the 30 ml syringe.
4. Draw 4 ml of WB into a 10 ml Luer-lock syringe, press the plunger to allow WB pass through the column. Unscrew the 10 ml syringe.
5. Draw 4 ml of 100% Ethanol into a 10 ml syringe, press the plunger to allow the ethanol pass through the column.
6. Unscrew the cap of MOE device from the 50 ml centrifuge tube and placed on a new 50 ml tube. Allow air-dry ethanol residue in the column completely.

Example 4—Elution of the Extracted cfDNA with 3 Methods

In this experiment, 3 elution methods were compared. Twelve MOE devices with extracted cfDNA from pooled plasma were divided into 3 groups (n=4): a) elution by high-speed centrifugation (HC); b) elution by air purging (AP) and c) elution by repellent fluids (RF).

The efficiency of recovery was compared with the eluted volume and cfDNA concentration in the elutes by qPCR assay for fragmented cfDNA of a house keeping gene B2M.

Extraction protocol HC: detach the filter column from the cap of MOE device and place the column in a 1.5 ml collection centrifuge tube, add 100 μl of EB on the matrix, seal the column with a screw cap on top, wait for 10 min for release. Then the collection tube was centrifuged at 12,000 g for 3 min.

Extraction protocol AP: add 100 μl of EB on the matrix through inlet port of the cap in the MOE device by pipetting and wait for 10 min. Connect a 10 ml syringe on the port of the cap, place the filter column with the cap on a 1.5 ml collection tube and purge the column by repeatedly pushing and drawing of the syringe plunger. The collection tube was centrifuged to collect the purged EB into the bottom of the tube.

Extraction protocol RF: add EB as described in protocol AP. After 10 min, a 5 ml syringe with 0.5 ml RF (PSF-10cSt Pure Silicone Fluid, Clearco Products, PA) was connected on the port of the cap and the column was placed on the collection tube. The plunger was pressed slowly to purge out EB and RF. A clear interface between EB (bottom) layer and RF layer was formed rapidly without centrifugation.

Quantification of cfDNA in the elutes. 10 µl of the elutes was removed as template for qPCR assay (SIBO qPCR mix, Occam Biolabs, Inc., DE). The residue elutes were carefully removed from the collection tubes and weight by a 0.1 mg grade digital balance. The results were shown in Table 1.

TABLE 1

| Protocol | Sample ID | Residue Elute weight (mg) |
|---|---|---|
| HC protocol | HC-1 | 85.2 |
|  | HC-2 | 83.4 |
|  | HC-3 | 76.5 |
|  | HC-4 | 81.7 |
| mean (+/−SD) |  | 81.7 (3.7) |
| AP protocol | AP-1 | 68.5 |
|  | AP-2 | 55.7 |
|  | AP-3 | 72.8 |
|  | AP-4 | 58.2 |
| mean (+/−SD) |  | 63.8 (8.2) |
| RF protocol | RF-1 | 82.2 |
|  | RF-2 | 74.1 |
|  | RF-3 | 83.8 |
|  | RF-4 | 76.7 |
| mean (+/−SD) |  | 79.2 (4.6) |

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A system for collecting biomolecules, the system comprising:
   an extractor assembly comprising a top cap, an extractor core, an extractor core adaptor, an extractor body having an internal volume, and a bottom cap ring;
   the top cap adapted to be removably secured to the extractor body with the bottom cap ring, the top cap having an internal side facing the internal volume of the extractor body and an external side facing away from the extractor body, the top cap comprising a sample connection port communicating between the internal side and the external side, the cap comprising no other orifices communicating between the internal side and the external side, the sample connection port comprising a first interlocking component for releasably locking the sample connection port to a cooperating second interlocking component, the internal side of the cap comprising a connection interface in fluid communication with the sample connection port;
   the extractor core adapted to be removably attached to the connection interface of the top cap, the extractor core having an open upstream end, an open downstream end, and an internal passage therebetween containing a substrate for collecting the biomolecules;
   the extractor body having a first open end configured to mate with the top cap, and a second end comprising an opening configured to receive the extractor core adaptor; and
   the extractor core adaptor having an upstream open end for mating with the downstream end of the extractor core, a downstream protrusion configured to project through the opening in the extractor body, a downstream open end, and an internal passage between the upstream open end and the downstream open end.

2. The system of claim 1, further comprising a syringe comprising the second interlocking component adapted to connect to the first interlocking component of the sample collection port in the top cap.

3. The system of claim 1, further comprising a shipping container defining a volume adapted to contain the extractor core, the shipping container adapted to releasably engage the extractor core for detaching it from the connection interface of the top cap, the shipping container further comprising a removable lid for temporarily sealing the extractor core within the shipping container.

4. The collection system of claim 1, wherein the extractor core substrate comprises a filter, a frit upstream of the filter, and a retaining ring downstream of the filter.

5. The collection system of claim 1, wherein the sample connection port protrudes from the external side of the top cap.

6. The collection system of claim 5, wherein the sample connection port first interlocking component comprises one end of a Luer lock fitting.

7. The collection system of claim 1, wherein the extractor core comprises a first component of a threaded interface and the top cap comprises a second component of the threaded interface, wherein the extractor core further comprises a first member disposed on an external surface thereof adapted to be releasably engaged by a cooperating second member disposed on an internal surface of the shipping container, the second member adapted to transmit force to the first member when a torsional force is applied to the extractor core in a direction for unscrewing the extractor core from its threaded connection with the top cap.

8. The collection system of claim 1, further comprising one or more sample processing, reagent, or waste collection containers, one or more of said containers comprising a flexible container having an expandable volume.

9. The collection system of claim 8, wherein the one or more said flexible containers comprises a plastic bag.

10. The collection system of claim 8, wherein the one or more flexible containers comprises one or more rigid stiffeners integrated into the bag for providing structural strength to the bag.

11. The collection system of claim 8, wherein the one or more flexible containers comprises a sample processing container having a sealing cap and an opening in the cap sized to receive a length of tubing inserted through the sealing cap in fluid communication with an inside of the flexible container.

12. The collection system of claim 11, further comprising a syringe comprising the second interlocking component adapted to connect to the first interlocking component of the sample collection port in the top cap, the length of tubing inserted through the sealing cap of the flexible container having a first end disposed inside the flexible container, and a second end comprising a first interlocking component adapted to connect to the second interlocking component of the syringe.

13. The collection system of claim 12, wherein the opening in the sealing cap is further sized to receive the downstream end of the extractor adaptor.

14. A method for collecting a sample of biomolecules, the method comprising the steps of:
   (a) providing the system for collecting biomolecules of claim 12;
   (b) collecting a volume of sample-containing fluid in the syringe;
   (c) connecting the syringe to the extraction assembly via the sample collection port and connecting the downstream end of the extractor adaptor to the sealing cap of the sample processing container; and
   (d) passing the volume of sample-containing fluid from the syringe through the extractor core, thereby collecting the sample on the substrate and collecting a remainder in the sample processing container, and optionally repeating this step one or more times, and optionally performing one or more washing steps.

15. The method of claim 14, wherein the system for collecting biomolecules further comprises a shipping container defining a volume adapted to contain the extractor core, the shipping container adapted to releasably engage the extractor core for detaching it from the connection interface of the top cap, the shipping container further comprising a removable lid for temporarily sealing the extractor core within the shipping container, the method further comprising the steps of:
   (e) placing the shipping container open end over the extraction core, engaging the extraction core with the shipping container, and detaching the extraction core from the top cap;
   (f) temporarily sealing the shipping container with the removable lid.

16. The method of claim 15, further comprising transporting the shipping container under ambient, non-climate-controlled conditions.

17. The method of claim 14, further comprising collecting the sample from the substrate, wherein said collecting comprises treating the sample on the substrate with an eluting buffer, injecting a repellent agent into the extractor core, and collecting the resulting combination of eluting buffer, repelling agent, and biomolecules.

18. The method of claim 14, comprising processing the biomolecules collected in the extraction core for detection of a disease.

19. The method of claim 18 wherein the disease is tuberculosis.

20. The method of claim 14, wherein the sample-containing fluid comprises plasma or serum.

* * * * *